United States Patent [19]
Hochmair et al.

[11] 4,441,210
[45] Apr. 3, 1984

[54] TRANSCUTANEOUS SIGNAL TRANSMISSION SYSTEM AND METHODS

[76] Inventors: Erwin S. Hochmair; Ingeborg J. Hochmair, both of A-1130 Wien Jaunerstrasse 27, Vienna, Austria

[21] Appl. No.: 303,590

[22] Filed: Sep. 18, 1981

[51] Int. Cl.³ .................. H04B 5/00; H04R 25/00
[52] U.S. Cl. .................... 455/41; 179/107 E; 179/107 BC; 324/207; 455/67
[58] Field of Search ............ 455/41, 67; 179/82, 179/107 BC, 107 E; 128/1.5, 419 PG, 419 PT; 333/177, 180; 324/207, 208, 55; 334/61; 336/115, 129

[56] References Cited

U.S. PATENT DOCUMENTS

| | | | |
|---|---|---|---|
| 2,182,071 | 12/1939 | Crossley | 333/180 |
| 3,209,081 | 9/1965 | Ducote | 179/107 BC |
| 3,357,434 | 12/1967 | Abell | 336/221 |

*Primary Examiner*—Marc E. Bookbinder
*Attorney, Agent, or Firm*—Flehr, Hohbach, Test, Albritton & Herbert

[57] ABSTRACT

Greater positioning tolerance is permitted in inductively coupled transmitter and receiver tuned circuits by achieving critical coupling therebetween. Critical coupling at a predetermined distance is obtained by selecting the appropriate quality, Q, of the tuned circuit, whereby the quality of the transmitter tuned circuit is preferably three times larger than the quality of the receiver tuned circuit. In a transcutaneous signal transmission system the critical coupling is realized by adjusting the spacing of the coils of the tuned circuits whereby the output impedance of the transmitter decreases to one-half the output impedance with no coupling.

11 Claims, 5 Drawing Figures

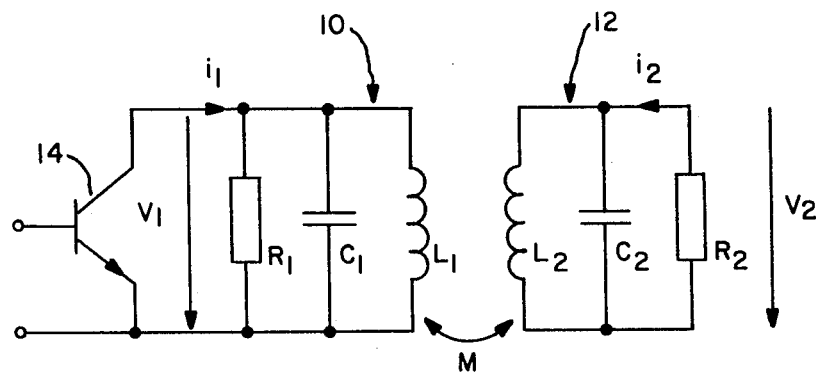
FIG.—1
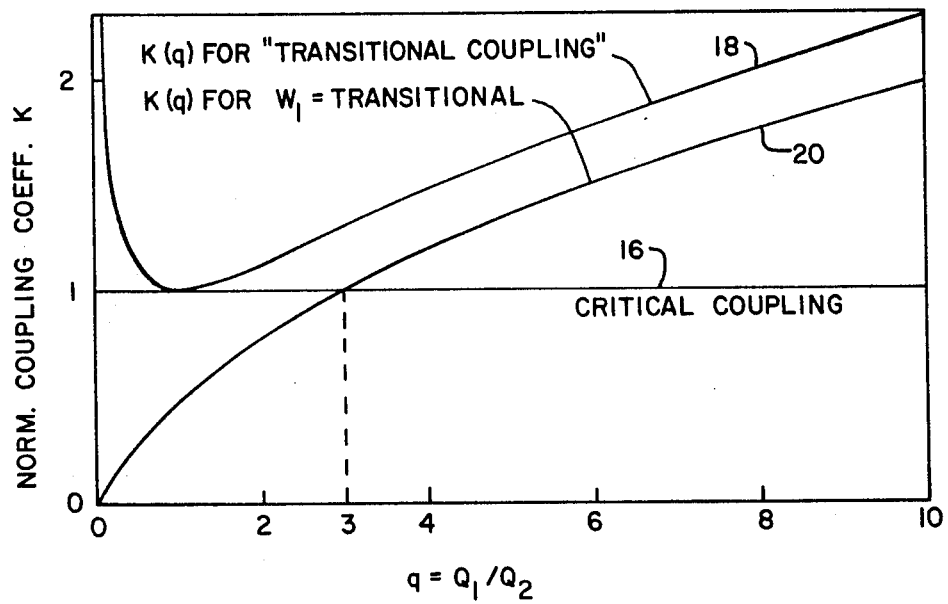
FIG.—2

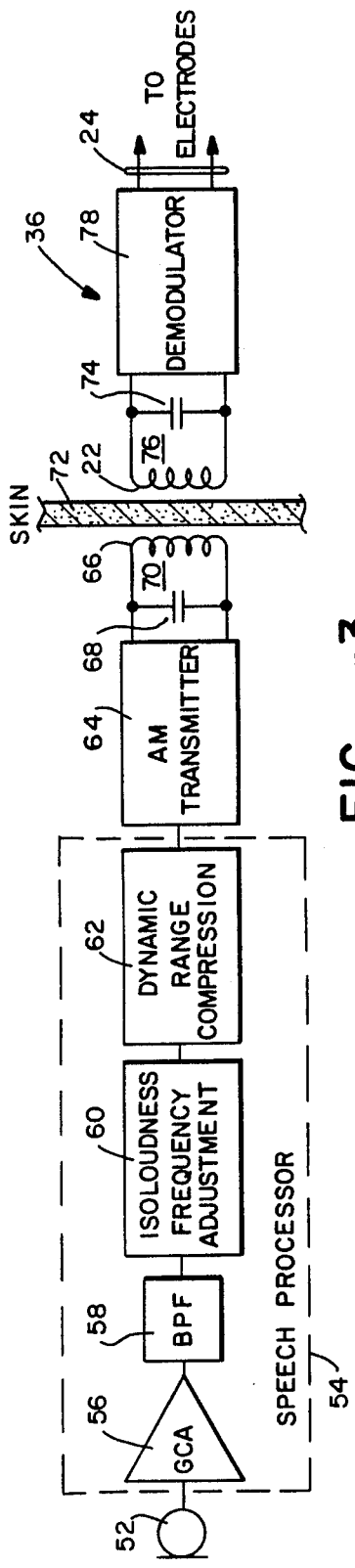
FIG.—3
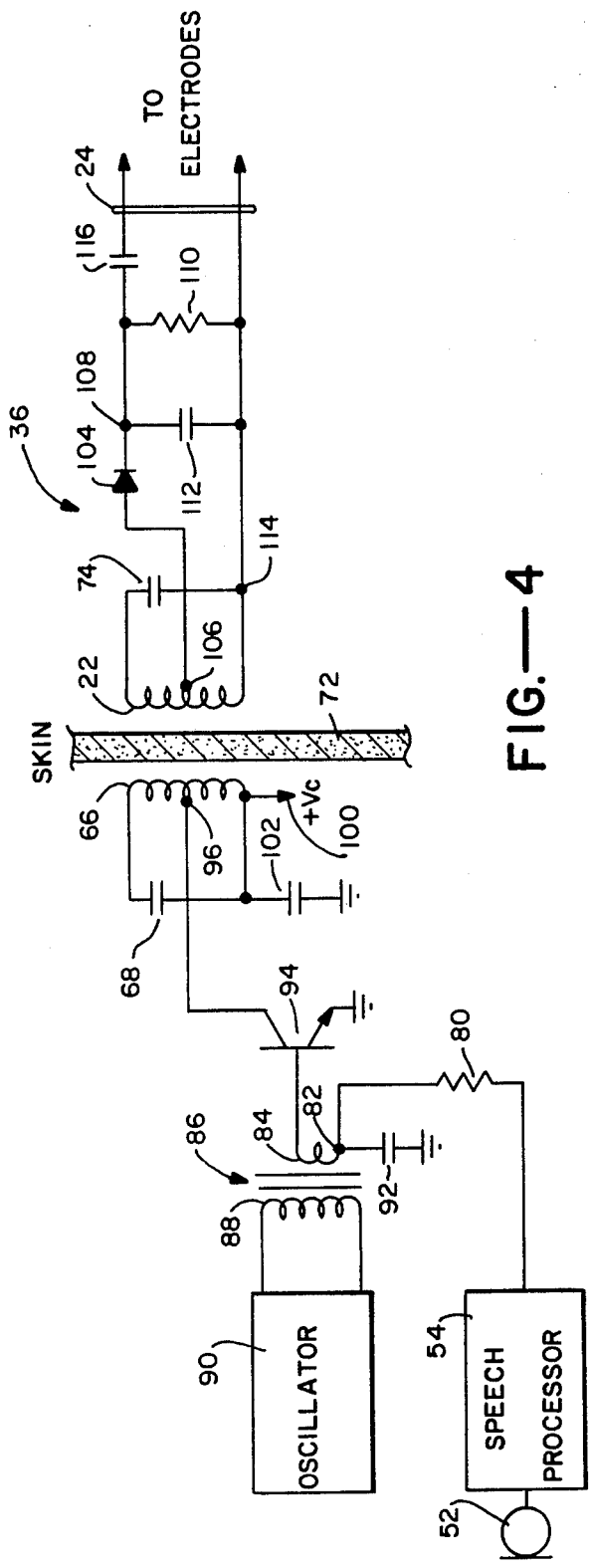
FIG.—4

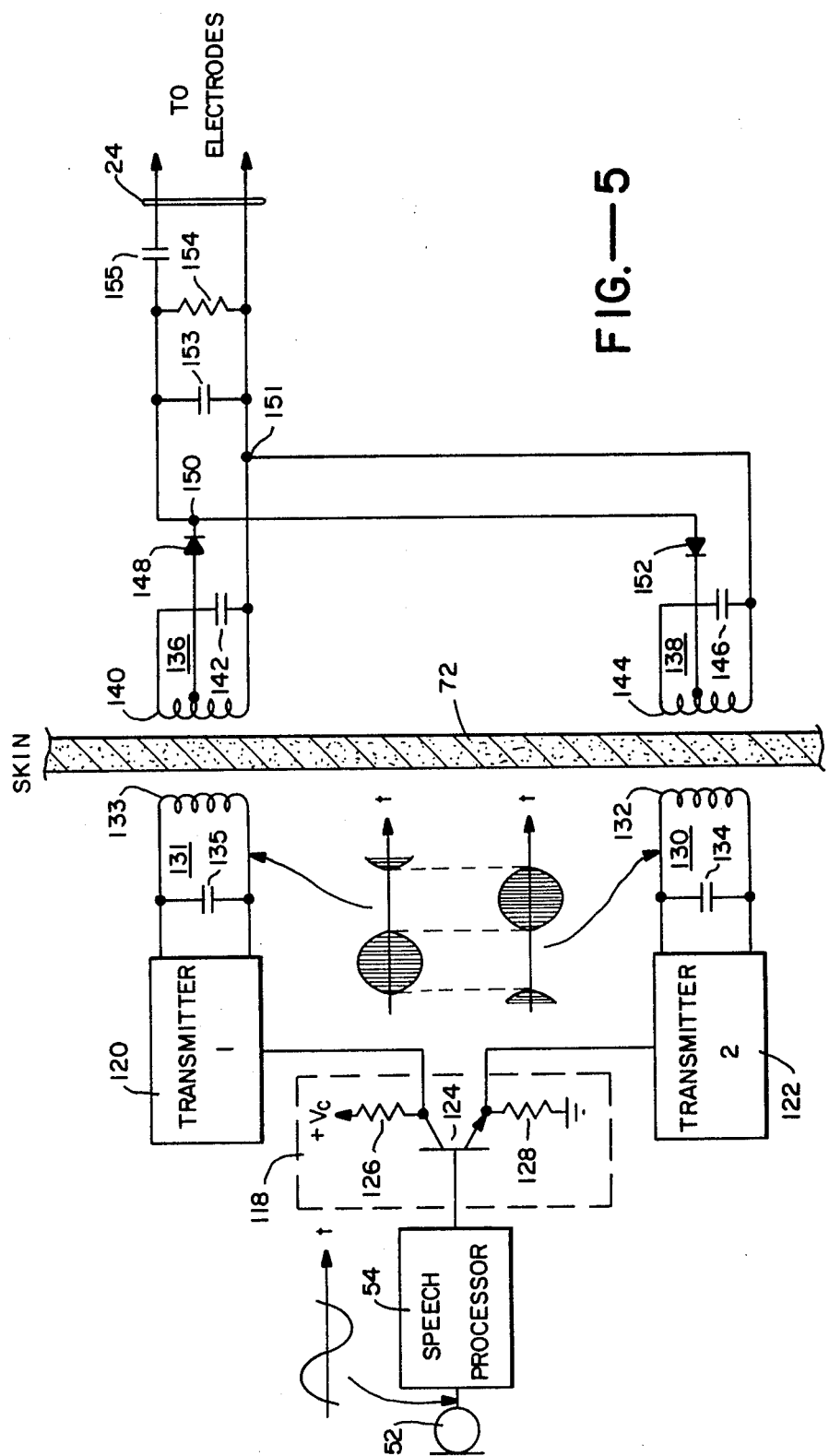
FIG.—5

TRANSCUTANEOUS SIGNAL TRANSMISSION SYSTEM AND METHODS

This invention relates generally to systems for transmitting electrical signals into the body of a patient, and more particularly the invention relates to the transmission of signals to a receiver which is implanted in the body.

Transcutaneous signal transmission systems are known and widely utilized for neural and muscle stimulation. Such systems are generally preferred over other transmission systems such as the use of implanted batteries or the use of direct percutaneous wiring. Typically, a transmitter transmits a modulated signal to the implanted receiver via two inductively coupled coils. The coils are part of tuned circuits which can cooperatively function as a band pass filter.

Our U.S. Pat. No. 4,284,856 and our co-pending patent application Ser. No. 267,405, filed May 26, 1981, now U.S. Pat. No. 4,357,497, disclose autitory stimulation apparatus in which inductively coupled coils are utilized for transcutaneous signal transmission.

Heretofore, inductive transmission systems have been designed for optimum efficiency with a consequential dependence of induced voltage in the implanted coil on exact positioning of the transmitter coil. Thus, in applications such as auditory stimulation where a precise output signal is necessary, the inductive transmission system has limitations in effectiveness.

Accordingly, an object of the present invention is an improved transcutaneous signal transmission system which utilizes inductively coupled coils.

Another object of the invention is the use of inductively coupled coils in a transcutaneous transmission system which have improved relative position tolerance.

Still another object of the invention is an improved method of transmitting signals by inductively coupled coils.

Briefly, in accordance with the invention a transcutaneous signal transmission system in which signals are transmitted from a transmitter means outside of a patient to a receiver means which is implanted in the patient is characterized by a first tuned circuit in the transmitter means and a second tuned circuit in the receiver means which are positioned to achieve essentially critical coupling with optimal displacement tolerance of the first and second tuned circuits.

The positioning tolerance of the transmitter tuned circuit couplling coil with respect to the receiver tuned circuit coupling coil for achieving essentially critical coupling of the two coils is enhanced by providing a transmitter tuned circuit and a receiver tuned circuit having quality values, Q, greater than 5 with the transmitter tuned circuit having a quality preferably 3 times larger than the receiver tuned circuit. In case the transmitter tuned circuit is at parallel tuned circuit it is preferably driven by an unsaturated current source. Critical coupling can be determined by measuring the load resistance of the transmitter when not loaded by the receiver and then placing the transmitter coil with respect to the receiver coil so that the load resistance of the transmitter decreases to one-half of the unloaded case. Load resistance can best be measured by observing the rf collector voltage of the output transistor.

The invention and objects and features thereof will be more readily apparent from the following detailed description and appended claims when taken with the drawings, in which:

FIG. 1 is a generalized schematic of a transcutaneous signal transmission system.

FIG. 2 is a plot of coil coupling factor (normalized) vs. circuit symmetry in terms of tuned circuit quality factors, Q.

FIG. 3 is a block diagram of an auditory stimulation system in accordance with the invention.

FIG. 4 and FIG. 5 are electrical schematics of two embodiments of stimulation system shown in FIG. 3.

Referring now to the drawings, FIG. 1 is a generalized electrical schematic of a transcutaneous signal transmission system comprising a transmitter tuned circuit shown generally at 10 and a receiver tuned circuit showing generally at 12. The transmitter tuned circuit 10 is driven by an RF amplifier transistor 14 and comprises resistor R1, capacitor C1 and inductor L1 all connected in parallel. The receiver tuned circuit comprises inductor L2, capacitor C2, and a load resistor R2 all connected in parallel. The two coils L1, L2 have a mutual inductance designated M.

The coupling coefficient of the 2 coils can be described in terms of the mutual inductance M and the inductances L1 and L2 as follows:

$$k = M/(L1 \cdot L2)^{\frac{1}{2}}$$

In the case of the two coils being incorporated in tuned circuits of qualities Q1 and Q2, respectively, thus forming a band pass filter as shown in FIG. 1, the coupling coefficient may be normalized as follows:

$$K = k(Q1 \cdot Q2)^{\frac{1}{2}} = (Q1 \cdot Q2)^{\frac{1}{2}} \cdot M/(L1 \cdot L2)^{\frac{1}{2}}$$

Critical coupling refers to a band pass filter consisting of two tuned circuits being driven by a current source, and at critical coupling the output voltage reaches a maximum. The output voltage is lower for both increased coupling, or overcoupling, and for decreased coupling, or undercoupling. Critical coupling occurs at $K = 1$ independent of the respective quality factors (Q) of the tuned circuits. Critical distance, as used herein, is the space between a transmitter coil and receiver coil at which critical coupling occurs.

Transitional coupling is the amount of coupling necessary to obtain a transition of the transimpedance of the two coils from a shape with one maximum to a shape possessing two maxima. As will be illustrated in FIG. 2, the coupling coefficient, K, for transitional coupling depends on the ratio of a qualities of the two coils, or $q = Q1/Q2$.

FIG. 2 is a plot of normalized coil coupling factor K vs. circuit symmetry in terms of the tuned circuit quality factors Q1 and Q2. From this graph it is noted that critical coupling occurs at $K = 1$ independent of the respective Q's of the tuned circuits, as illustrated by the straight line 16. Curve 18 is a plot of the transitional coupling which is necessary to obtain a transition of the absolute value of the transimpedance from a shape with one maximum to a shape having two maxima. As noted by curve 18 transitional coupling is dependent on the quality factors. The input transitional coupling or the amount of coupling necessary to obtain a transition of the absolute value of the frequency dependent input impedance is illustrated by curve 20. Input transitional coupling is also dependent on the quality of the coupled coils. From FIG. 2 it is seen that for $q = 3$, or $Q1 = 3Q2$ the frequency dependent transimpedance goes from one maximum to two maxima, also indicating critical coupling.

By designing the transcutaneous signal transmission system with critical coupling of the tuned circuits, the dependence of the induced voltage in the implanted coil on coil separation shows a flat maximum. In the vicinity of critical distance the coupling may be changed by varying the spacing or the lateral displacement to some extent with only minor changes in output voltage. Thus, the transmission system is optimized for position tolerance.

Consider now FIG. 3 which is a block diagram of auditory stimulation apparatus in accordance with the invention and FIGS. 4 and 5 which are schematic diagrams of specific embodiments of the system of FIG. 3.

In FIG. 3 a microphone 52 has its output applied to speech processor electronics shown as being enclosed by the broken line box 54. Included in the speech processor channel is a gain controlled amplifier 56 which receives as its input the electrical output from the microphone 52 and the output from the gain controlled amplifier 56 is applied through a band-pass filter 58 to a so-called isoloudness frequency adjustment circuit 60 which is a frequency dependent network which compensates for the fact that the simulated current for a given loudness is frequency dependent. The speech processor electronics 54 further includes a dynamic range compression circuit 62 which may either precede or follow the isoloudness frequency adjustment circuit 60.

The output from the speech processor 54 is arranged to modulate the output from an RF oscillator in the AM transmitter module 64. The modulated output from the transmitter is applied across a transmitting coil 66 and a capacitor 68, these last mentioned two components being designed to cooperate as a tuned circuit 70.

The implant unit 36 is shown to the right of the skin interface 72 and includes the receiver coil 22 which has a capacitor 74 connected in parallel with it. The parallel combination of the receiving coil 22 and the capacitor 74 forms a tuned receiver circuit 76. The output from the tuned receiver circuit is coupled as an input to a diode demodulator network 78 which functions in a conventional fashion to remove the modulation envelope from the RF carrier. The output from the diode demodulator is applied via the leads 24 to the active and indifferent electrode surfaces.

The construction and operation of the speech processor electronics 54 is fully set forth and described in our co-pending application Ser. No. 267,405, filed May 26, 1981, now U.S. Pat. No. 4,357,497, and, hence, it is believed unnecessary to explain that apparatus here. However, the construction of the AM transmitter module 64 will be described in greater detail with reference to the electrical schematic diagram of FIG. 4. In this figure, the microphone pick-up 52 and the speech processor module 54 connected to it are shown as being coupled through a resistor 80 to a first terminal 82 of the secondary winding 84 of a transformer indicated generally by numeral 86. The primary winding 88 of the transformer is coupled across the output of an RF oscillator 90.

The terminal 82 has a decoupling capacitor 92 connected between it and ground. This capacitor provides RF decoupling in a conventional fashion. The other terminal of the secondary winding 84 is connected directly to the base electrode of an NPN transistor 94.

The emitter electrode of the transistor is connected to ground and its collector electrode is tied to an intermediate terminal 96 of a transmitting coil 66. A capacitor 68 is connected directly in parallel with the entire transmitting coil 66 and the requisite DC bias voltage for the transmitter 94 is applied at terminal 100. A further RF decoupling capacitor 102 is connected between ground and the common junction of the coil 66 and the capacitor 68.

The implanted receiver module 36 comprises a receiving coil 22 and a tuning capacitor 74. The demodulator portion of the receiver comprises a semiconductor diode 104 having its anode connected to an intermediate terminal 106 on the receiving coil 22 and its cathode electrode connected to a junction point 108. A resistor 110 and a capacitor 112 are connected in parallel with one another between the junction point 108 and the outer terminal 114 of the coil 22. A blocking capacitor 116 is disposed in series between the junction point 108 and the active electrode. The second electrode is tied directly to the aforementioned junction point 114.

In operation, the modulation signal which is a speech derived, time varying wave, originates at the output of the speech processor 54 and is applied to the transistor modulator via resistor 80 as is the RF carrier from the oscillator 90 via the transformer coupled to the base of the transistor 94. The capacitor 92 as well as the capacitor 102 serve to decouple the RF signal from the DC supply. The collector of the modulation transistor 94 is connected to the tap of the tuned transmitter circuit which includes the coil 66 and the capacitor 68. The transmitter coil 66 inductively couples the modulated carrier signal to the implanted receiver coil 22 which, together with the capacitor 74, also comprises a tuned receiver circuit. The received signal is demodulated by the semiconductor diode 104 in a conventional fashion with capacitor 112 providing RF decoupling and resistor 110 providing the requisite DC path to ground. The capacitor 116 serves to block any DC current from reaching the electrodes.

The combination of the tuned transmitter circuit and the tuned receiver circuit comprise a band-pass filter network. It has been found that the stimulating voltage becomes highly independent of relative position between the transmitter coil 66 and the receiver coil 22 when the transmitter coil is positioned at the critical distance relative to the receiving coil. As above described the critical distance refers to the spacing between the transmitter and receiver coil at which critical coupling occurs. If the spacing is decreased from the critical distance, over-coupling results and, similarly, when the spacing between the two coils exceeds the critical distance, there is under-coupling. For a tuned band-pass filter, the effective critical coupling ensures a relatively stable output voltage over a coil spacing range which is in the vicinity of the critical distance.

The transimpedance, $r_m$, which is the ratio of the voltage across the receiver coil divided by the current flowing in the transmitter coil ($V_2/i_1$), however, determines the voltage induced in the receiver coil only where the transmitter winding is being driven by a current source. If saturation of the output transistor 94 occurs, the input voltage is kept constant and the induced voltage across the secondary (the receiver coil) is no longer determined by the transimpedance $r_m k$ but by the voltage gain which is found to linearly increase with the coupling coefficient K, and hence does not show a relative maximum. Thus, neither critical coupling nor a critical distance occur under this condition. Therefore, saturation of the output transistor 94 should be avoided over a range of coupling coefficients on either side of the critical coupling value. If saturation were to occur, the usable range of coupling coefficients is markedly decreased as is the attendant displacement tolerance of the transmitter and receiver coils.

In that the receiver is surgically implanted, it is practically impossible to obtain direct measurements at nodes within the receiver electronics once the implant surgery has taken place. The location of the transmitter coil to obtain critical coupling must therefore be deduced from measurements obtainable from the transmitter circuit.

It may also be shown that at the critical coupling, the input resistance looking into the terminals of the transmitting coil decreases to one-half of its value with no coupling at all. With this fact in mind, it is possible to deduce the optimum placement of the transmitter coil at the critical distance. Specifically, by applying a sufficiently low RF carrier level to the base of transistor 94 to safely preclude saturation of that transistor, the RF collector voltage of the transistor 94 may be measured while the transmitter coil is made to approach the implanted receiver coil. The distance necessary for a fifty percent reduction of the RF collector voltage with respect to its value at no coupling indicates positioning of the transmitter coil at the critical distance.

One approach [which is somewhat different from the technique where the transmitter coil voltage is monitored to note the 50% reduction] involves the observation of the swept input resistance, [i.e., the variation of the ratio of the input voltage to the input current as the transmitter coil is made to approach the receiver coil,] which undergoes an easily observable transition from one maximum to two maxima at critical coupling. This method offers the advantage in that it may be performed at the carrier level actually used in the transmission of speech modulated signals to the receiver. Another method involves the use of a reduced carrier level and, as such, could lead to somewhat inaccurate results if the output impedance of the RF amplifier used in the transmitter is voltage dependent. For this latter method to work, however, it is required that the Q of the transmitter tank circuit be approximately three times as large as the Q of the receiver's tank circuit.

In FIG. 4 the modulation signal from the speech processor 54 is applied to the base of the output transistor 94 by way of the transformer's secondary winding 84. By introducing the modulation signal on the base contact of the output transistor, (phase modulation), saturation is avoided. Where collector modulation is employed, however, this undesirable saturation could result. It is feasible, however, to introduce the modulation signal at the emitter electrode.

An alternative arrangement of an external speech processor and transmitter combination and an implantable receiver combination is illustrated in FIG. 5. Here, a single speech processor network 54 and a single set of stimulating electrodes 24 are interfaced with a dual transmission channel for performing transcutaneous stimulation. The microphone pick-up 52 provides its input to the speech processor 54 which, again, may be configured as set forth in the aforereferenced application Ser. No. 267,405, now U.S. Pat. No. 4,357,497. The modulation signal from the speech processor network 54 is applied to a phase splitter indicated generally by numeral 118 and from there to AM transmitters 120 and 122. The phase splitter is shown as including an NPN transistor 124 having its collector electrode coupled through a resistor 126 to a source of potential $V_c$. The emitter electrode of the transistor 124 is coupled through a resistor 128 to ground. The signal derived from the collector electrode of the transistor 124 is applied to the transmitter 120 while the signal appearing at the emitter electrode of transistor 124 is applied to the transmitter 122.

Transmitter 120 delivers its output to a tuned circuit 131 comprised of the transmitter coil 133 and parallel capacitor 135 while transmitter 122 provides its output to a similar tuned circuit 130 comprised of a transmitter coil 132 and a tuning capacitor 134. Implanted beneath the temporal muscle posterior to the patient's auricle is a receiver module including tuned circuits 136 and 138 which are inductively coupled to the transmitting tuned circuits 130 and 131, respectively. The tuned circuit 136 includes a receiving coil 140 and an associated tuning capacitor 142 while the tuned circuit 138 includes a receiving coil 144 and its associated tuning capacitor 146. The receiving coil 140 has an intermediate terminal and connected to that terminal is the anode electrode of a semiconductor diode 148. The cathode electrode of that diode is tied to a junction 150. An oppositely poled diode 152 is tied between the junction 150 and a terminal on the receiver coil 144. The lowermost terminals of the receiving coils 140 and 144 are tied together at a junction point 151. Connected between the junction points 150 and 151 is a parallel combination of an RF bypass capacitor 153 and a load resistor 154. The junction 150 is also coupled through a DC blocking capacitor 155 to the active electrode while the junction 151 is tied to the ground or other electrode.

The arrangement shown in FIG. 5 is used to stimulate only one particular site (the promontory or round window membrane) using the two electrodes of a single channel. However, it uses two transmission channels arranged to operate in a push-pull configuration. The advantage of using this push-pull arrangement is that the resistor 154 may be made very large (or even deleted) such that substantially all of the power transmitted to the implant reaches the electrode, neglecting of course the diode losses. It is thus possible to reduce input power by about a factor of four as compared to the single transmission channel device of FIG. 4.

The embodiment shown in FIG. 5 may be thought of as comprising two transmission channels, each being essentially equivalent to the single transmission channel of FIG. 4. With resistor 154 having a large value as compared to the electrode impedance, it will absorb any differential dc current resulting from any assymetry in the transmission characteristics of the two channels. It offers the further advantage in that it may function in the same fashion as the resistor 110 in FIG. 4 should only one channel be operative. Thus, this configuration increases reliability by offering an additional transmission channel in case one transmission channel is lost, albeit at a lower efficiency.

In the configuration of FIG. 5, the transmitters are modulated by signals 180 degrees out of phase. These modulation signals are obtained from a phase splitter 118 which is driven by the audio signal obtained from the microphone 52 by way of the speech processor 54.

Those skilled in the art will recognize that instead of constructing the band-pass filter using two tuned parallel resonant circuits as in the embodiment of FIGS. 4 and 5, it is also possible to implement the band-pass filter with one series tuned circuit and one parallel tuned circuit. In such a case, the input of the band-pass filter should not be current driven, but rather voltage driven, in order to obtain a relative maximum of the induced voltage at the point of critical coupling. In the arrangement where the series tuned circuit forms a port of the transmitter, the output transistor preferably works in the saturated condition and may be modulated by collector modulation. Where the series tuned circuit forms a part of the receiver electronics, however, the parallel tuned circuit of the transmitter should be driven by a non-saturated RF amplifier.

While the invention has been described with reference to specific embodiments, the description is illustrative of the invention and is not to be construed as limiting the invention. Various applications and modifications may occur to those skilled in the art without departing from the true spirit and scope of the invention as defined by the appended claims.

What is claimed is:

1. In a transcutaneous signal transmission system having an external transmitter and a living body-implanted receiver, a method for placing a first coupling coil of said transmitter with respect to a second coupling coil of said receiver to achieve critical coupling comprising the steps of driving said first coupling coil of said transmitter with an unsaturated current source, measuring the output voltage of said transmitter and adjusting the space between said first and second coupling coils whereby the output voltage of said transmitter decreases to one-half of the output voltage with no coupling.

2. The method as defined by claim 1 wherein said first coupling coil and said second coupling coil comprise respective parts of a first tuned circuit and a second tuned circuit, said first and second tuned circuits having qualities, Q, which are selected whereby critical coupling of said first and second coils is achieved at a spacing of sufficient width to bridge the skin barrier of a patient.

3. A method of enhancing the positioning tolerance of an external transmitter tuned circuit coupling coil with respect to a living body-implanted receiver tuned circuit coupling coil and achieving essentially critical coupling of said transmitter coupling coil and said receiver coupling coil wherein the transmitter tuned circuit and the implanted receiver tuned circuit having quality values greater than five with said transmitter tuned circuit having a quality on the order of at least 3 times that of said receiver tuned circuit, comprising the steps of: driving said transmitter tuned circuit with an unsaturated current source, measuring an output voltage of said transmitter, and positioning said transmitter coupling coil with respect to said receiver coupling coil until the output voltage of said transmitter is on the order of one-half of the unloaded output voltage of said transmitter.

4. A transcutaneous signal transmission system in which auditory signals are transmitted from a transmitter means outside of a patient to a receiver means implanted in the patient characterized by a first tuned circuit of said transmitter means and a second tuned circuit of said receiver means being positioned to achieve essentially critical coupling with optimal displacement tolerance of said first and second tuned circuits.

5. A transcutaneous signal transmission system as defined by claim 4 wherein said first and second tuned circuits cooperatively function as a current driven band-pass filter.

6. A transcutaneous signal transmission system as defined by claim 4 or 5 wherein each of said tuned circuits has a quality factor greater than 5.

7. A transcutaneous signal transmission system as defined by claim 6 wherein the quality of said first tuned circuit is at least 3 times greater than the quality of said second tuned circuit.

8. A transcutaneous signal transmission system comprising:
    transmitter means located externally of a living body including a first carrier signal generator, a modulation signal generator, a first modulator for modulating a carrier signal from said first carrier signal generator with a modulation signal and including a first non-saturating RF output transistor, and a first tuned circuit including a first inductor for receiving an amplified modulated carrier signal from said first output transistor,
    receiver means implanted in said body and comprising a second tuned circuit including a second inductor and a detector, and
    said first tuned circuit and said second tuned circuit cooperatively functioning as a band-pass filter with said first and second inductors being positioned to achieve essentially critical coupling with optimal displacement tolerance of said first and second tuned circuits.

9. A transcutaneous signal transmission system as defined by claim 8 wherein said transmitter means further includes a second carrier signal generator, a second modulator for modulating a carrier signal from said second carrier signal generator with a modulation signal and including a second non-saturating RF output transistor, a third tuned circuit including a third inductor for receiving an amplified modulated carrier signal from said second output transistor, phase splitting means coupling said modulation signal to said first and second modulators in phase opposition, said first and third tuned circuits being connected to be driven individually by said first and second modulators, respectively.

10. A transcutaneous signal transmission system as defined by claim 9 wherein said receiver means further includes a fourth tuned circuit positioned to be critically coupled with said third tuned circuit of said transmitter means and wherein said receiver means further includes a pair of oppositely poled diode rectifiers serially connected between said second and fourth tuned circuits and having a junction point, and a parallel resistance-capacitance load connected to said junction point.

11. In a transcutaneous signal transmission system having an external transmitter and an implanted receiver, a method for placing a first coupling coil of said transmitter with respect to a second coupling coil of said receiver to achieve critical coupling comprising the steps of driving said first coupling coil of said transmitter with an unsaturated current source, measuring output voltage of said transmitter, and moving said first coupling coil with respect to said second coupling coil until the output voltage of said transmitter decreases to one-half of the output voltage with no coupling of said first coupling coil and said second coupling coil.

* * * * *